(12) United States Patent
Lange

(10) Patent No.: US 6,762,332 B2
(45) Date of Patent: Jul. 13, 2004

(54) PROCESS FOR PREPARING AN ALCOHOL FROM AN OLEFIN

(75) Inventor: Jean-Paul Lange, Amsterdam (NL)

(73) Assignee: Shell Oil Company, Houston, TX (US)

( * ) Notice: Subject to any disclaimer, the term of this patent is extended or adjusted under 35 U.S.C. 154(b) by 36 days.

(21) Appl. No.: 10/239,100

(22) PCT Filed: Mar. 22, 2001

(86) PCT No.: PCT/EP01/03276

§ 371 (c)(1),
(2), (4) Date: Nov. 22, 2002

(87) PCT Pub. No.: WO01/70660

PCT Pub. Date: Sep. 27, 2001

(65) Prior Publication Data

US 2004/0039236 A1 Feb. 26, 2004

(30) Foreign Application Priority Data

Mar. 22, 2000 (EP) .............................. 00302361

(51) Int. Cl.$^7$ ................................ C07C 29/16

(52) U.S. Cl. ................. 568/883; 568/814; 568/909
(58) Field of Search ............................ 568/883, 909, 568/814

(56) References Cited

U.S. PATENT DOCUMENTS

| | | | | |
|---|---|---|---|---|
| 3,839,459 A | * | 10/1974 | Bennett | ............... 568/454 |
| 4,447,661 A | * | 5/1984 | Hoshiyama et al. | ........ 568/882 |
| 4,982,011 A | | 1/1991 | Hanin | |
| 5,096,688 A | | 3/1992 | Miller et al. | |
| 5,364,984 A | | 11/1994 | Arntz et al. | |
| 6,548,716 B1 | * | 4/2003 | Lange | ............... 568/862 |

FOREIGN PATENT DOCUMENTS

| WO | 94 06739 | 3/1994 | ........... C07C/29/16 |

\* cited by examiner

*Primary Examiner*—Michael L. Shippen

(57) ABSTRACT

A process for the preparation of an alcohol from an olefin wherein the olefin is reacted with syngas in the presence of a catalyst system having a homogeneous hydroformylation catalyst and a heterogeneous catalyst having copper on a support.

16 Claims, No Drawings

PROCESS FOR PREPARING AN ALCOHOL FROM AN OLEFIN

FIELD OF THE INVENTION

The present invention relates to a process for preparing an alcohol from an olefin, wherein the olefin is reacted with syngas in the presence of a hydroformylation catalyst.

BACKGROUND OF THE INVENTION

The synthesis of "oxo" alcohols by hydroformylating an olefin followed by the hydrogenation thereof is known. As described in Chapter 1 of Falbe's "New Syntheses with Carbon Monoxide" (Springer-Verlag, 1980), the synthesis involves the preparation of an aldehyde by the following reaction:

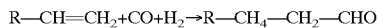

The hydroformylation reaction is typically conducted in the presence of a homogeneous catalyst on the basis of a transition metal, such as cobalt, nickel, palladium or platinum. This reaction is also extensively described in Chapter 4 of "Carbonation" by Colquhoun et al (Plenum Press, 1991).

A secondary reaction occurring simultaneously involves the hydrogenation of the oxo-aldehyde into an oxo-alcohol. The extent of this secondary reaction can be increased via various measures, although it must be borne in mind that these measures may lead to many undesirable side-products (Falbe, Chapter 1.5.2.2.1).

Some homogeneous catalysts have sufficient activity to hydrogenate the in-situ formed oxo-aldehyde into the desired oxo-alcohol. However, in most instances a separate post-hydrogenation finishing step of the oxo-alcohol is essential due to quality considerations. It therefore remains desirable to be able to produce alcohols in a single-step process without the necessity of a post-hydrogenation finishing step.

SUMMARY OF THE INVENTION

Accordingly, the present invention provides a process for the preparation of an alcohol from an olefin, wherein the olefin is reacted with syngas in the presence of a catalyst system comprising a homogeneous hydroformylation catalyst and a heterogeneous catalyst comprising copper on a support.

DETAILED DESCRIPTION OF THE INVENTION

Hydroformylation of an olefin in the presence of a homogeneous transition metal catalyst is well documented. Such processes rely for instance on classical catalysts such as Co—, Rh—, Ir—, Ru— or Os—carbonyls, or on modified catalysts (e.g., wherein the CO ligands are replaced by phosphines). Of particular interest are modified palladium or platinum hydroformylation catalysts.

The process of the present invention comprises the modification of such hydroformylation processes by conducting the hydroformylation in the presence of a catalyst system comprising a known homogeneous hydroformylation catalyst and a heterogeneous catalyst comprising copper on a support.

The process of the present invention involves using a catalyst system further comprising a supported copper catalyst. The catalyst comprising copper on a support is believed to be at least partially in a metallic state under operating conditions. The catalyst may be a sophisticated catalyst wherein the copper is part of an alloy, and/or wherein the catalyst comprises additional, promoter, metals. Suitable alloys can include one or more metals of Groups 8 to 11 of the Periodic Table of Elements. Suitable promoter metals can include one or more metals of Groups 1 to 7 of the Periodic Table. However, ordinal catalyts, based on copper as the only active components, are quite acceptable.

The nature of the catalyst support is not essential. Suitable supports include inert carriers composed of a metallic or glass sponge, or based on an organic carbide, or oxide, or carbon. For instance, the support may be based on oxides of Groups 2–6 and 12–14 metal of the Periodic Table and mixtures thereof e.g. ZnO, titania, alumina, zirconia, silica and/or zeolites. Preferred supports are resistant to an acidic medium. Suitable results in model reactions have been achieved with copper on ZnO, on silica, and on $Cr_2O_3$.

The support may be used as fine powder or shaped into mouldings such as, for example, pellets, granules, or extrudates using methods known in the art, such as those described in U.S. Pat. No. 5,364,984 which disclosure is herein incorporated by reference. Alternatively, the support may be in the shape of a honeycomb, a foam, a sponge or similarly large monolith.

The amount of copper may also vary widely. For instance, the copper may be present on the support in a quantity of 0.1 to 80 w %, preferably 10 to 50 w %, more preferably 25 to 35 w %, relative to the support.

The synthesis of the copper catalyst is conventional, typically involving the co-precipitation of copper and support precursor. Optionally it can also be prepared by doping a carrier with a copper solution, calcining the loaded carrier, and reducing the same at elevated temperatures under $H_2$. Various supported copper catalyst are commercially available, e.g. for use in the hydrogenation of esters to the corresponding alcohols. Copper containing catalysts are also described in U.S. Pat. No. 5,096,688, in a two-stage process for converting synthesis gas into higher alcohols. This document describes its use for the hydrogenation of undesirable non-alcohol oxygenates and the conversion of water and carbon monoxide in hydrogen gas and carbon monoxide.

The process of the present invention may be a continuous process, a semi-continuous process of a batch process. In the case of continuous processes, liquid hourly space velocities of about 0.1 to about 10 $h^{-1}$ are preferred. In batch processes, reaction times varying from about 0.1 to about 10 hours are suitable. The quantity in which the supported copper catalyst may be used, in batch processes, may vary widely, e.g. ranging from about 0.1 to about 50 w %, preferably from about 1.0 to about 10 w %, calculated on the weight of the olefin.

Feed and process conditions are entirely conventional. By way of example, the feed may be an olefin or substituted olefin of 2 to 20 carbon atoms, which may be linear, branched or cyclic. The hydrogenation conditions are not very critical. The temperature may vary widely, e.g. from about 10 to about 300° C., preferably from about 20 to about 150° C. Similarly, the pressure may vary from about atmospheric to about 30 MPa (300 bar), preferably from about 0.5 to about 7 MPa (5 to 70 bar). The hydroformylation catalyst is employed in conventional quantities too, varying from about 0.001 to about 10.0 mmole per mole olefin. The process may involve the use of a solvent.

Synthesis gas is a blend of hydrogen and carbon monoxide. It typically is made by partial combustion of a petroleum feed. Commercial syngas comprises hydrogen and carbon monoxide in an $H_2/CO$ ratio of about 1.0–2.0. Syngas with a higher $H_2/CO$ ratio, e.g. up to about 10.0, and higher, may be prepared by the so-called water gas shift reaction, and such gases may also be used in the process of the present invention. On the other hand, it is an advantage of the present invention that it may cope with carbon monoxide-rich gases, at $H_2/CO$ ratios as low as about 0.5. The preferred $H_2/CO$ ratio hence varies from about 0.5 to about 10.0, more preferably from about 1.0 to about 5.0.

Preparation of Nonanol

In the following example a hydrogenation catalysts as hereafter described may be used which are provided for illustrative purposes and are not to be construed as limiting the invention.

Cu/Zn a ZnO/alumina catalyst containing~40 w % of Cu
Cu/Si a silica catalyst containing~29 w % of Cu
Cu/Cr a chromite catalyst containing~37 w % of Cu Prior to the reaction, the hydrogenation catalyst should be reduced, for instance, at 300° C. for 11 hours under 0.5 MPa (5 bar) $H_2$.

Charge a 250 ml magnetically-stirred autoclave with 20 ml 1-octene, 50 ml 2,5,8-trioxanonane, 0.25 mmole of palladium acetate, 0.3 mmole of 1,3-bis(di-n-butyl-phosphino)propane, 2 mmole sodium trifluoroacetate, and 2 g of any of the above hydrogenation catalysts. After being flushed, pressurize the autoclave with carbon monoxide and hydrogen up to a partial pressure of 30 bar of each. Seal the autoclave, heat to a temperature of 90° C., and maintain at that temperature for 5 hours.

What is claimed is:

1. A process for the preparation of an alcohol from an olefin, wherein the olefin is reacted with syngas in the presence of a catalyst system comprising a homogeneous hydroformylation catalyst and a heterogeneous catalyst comprising copper on a support.

2. The process of claim 1 wherein the heterogeneous catalyst comprises metallic copper on a support.

3. The process of claim 1 wherein the support is comprised of a clay, a metallic or glass sponge, an inorganic carbide, or oxide or carbon.

4. The process of claim 3 wherein the heterogeneous catalyst is selected from Cu on ZnO, on alumina, on silica, or on $Cr_2O_3$.

5. The process of claim 1 wherein the copper is present on the support in an amount of 0.1 to 80 w % relative to the support.

6. The process of claim 1 wherein the (substituted) olefin has 2 to 20 carbon atoms, and is either linear, branched or cyclic.

7. The process of claim 2 wherein the support is comprised of a clay, a metallic or glass sponge, an inorganic carbide, or oxide or carbon.

8. The process of claim 2 wherein the copper is present on the support in an amount of 0.1 to 80 w % relative to the support.

9. The process of claim 4 wherein the copper is present on the support in an amount of 0.1 to 80 w % relative to the support.

10. The process of claim 5 wherein the support is based on oxides of Group 2–6 and Group 12–14 metal of the Periodic Table and mixtures thereof.

11. The process of claim 10 wherein the cooper is present on the support in an amount of 0.1 to 80 w % relative to the support.

12. The process of claim 10 wherein the support is selected from the group consisting of ZnO, titania, alumina, zirconia, silica, or zeolites and mixtures thereof.

13. The process of claim 12 wherein the cooper is present on the support in an amount of 10 to 50 w % relative to the support.

14. The process of claim 1 wherein the catalyst comprises copper on ZnO, on silica or on $Cr_2O_3$.

15. The process of claim 1 wherein the syngas has a $H_2/CO$ ratio from 0.5 to 10.0.

16. The process of claim 14 wherein the copper is present on the support in an amount of 0.1 to 80 w % relative to the support.

* * * * *